(12) United States Patent
Ehman et al.

(10) Patent No.: US 7,991,449 B2
(45) Date of Patent: Aug. 2, 2011

(54) IMAGING ELASTIC PROPERTIES OF THE LUNG WITH MAGNETIC RESONANCE ELASTOGRAPHY

(75) Inventors: Richard L. Ehman, Rochester, MN (US); Kiaran P. McGee, Rochester, MN (US); Brian C. Goss, Wheaton, IL (US); Joel P. Felmlee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1132 days.

(21) Appl. No.: 11/407,759

(22) Filed: Apr. 20, 2006

(65) Prior Publication Data

US 2006/0264736 A1 Nov. 23, 2006

Related U.S. Application Data (60) Provisional application No. 60/674,818, filed on Apr. 26, 2005.

(51) Int. Cl.
*A61B 5/05* (2006.01)

(52) U.S. Cl. ........ 600/407; 600/409; 600/410; 324/306; 324/309; 324/308

(58) Field of Classification Search ............... 600/407, 600/409, 410; 324/306–309
See application file for complete search history.

(56) References Cited

U.S. PATENT DOCUMENTS

| | | | | |
|---|---|---|---|---|
| 4,341,222 A | * | 7/1982 | Gardineer et al. | 600/437 |
| 4,599,565 A | * | 7/1986 | Hoenninger et al. | 324/309 |
| 5,592,085 A | * | 1/1997 | Ehman | 324/309 |
| 5,789,921 A | | 8/1998 | Albert et al. | |
| 5,825,186 A | * | 10/1998 | Ehman et al. | 324/309 |
| 6,241,966 B1 | | 6/2001 | Albert et al. | |
| 6,338,836 B1 | | 1/2002 | Kuth et al. | |
| 6,370,415 B1 | | 4/2002 | Weiler et al. | |
| 6,589,506 B2 | | 7/2003 | Cremillieux et al. | |
| 6,593,144 B2 | * | 7/2003 | Albert et al. | 436/173 |
| 2001/0031242 A1 | | 10/2001 | Cremillieux et al. | |
| 2002/0043267 A1 | | 4/2002 | Weiler et al. | |
| 2002/0198449 A1 | | 12/2002 | Baumgardner et al. | |
| 2003/0023162 A1 | | 1/2003 | Baumgardner et al. | |
| 2004/0260173 A1 | * | 12/2004 | Salerno et al. | 600/420 |

* cited by examiner

*Primary Examiner* — Tse Chen
*Assistant Examiner* — Joel F Brutus
(74) *Attorney, Agent, or Firm* — Quarles & Brady LLP (57) ABSTRACT

A noble gas is administered to a subject to fill the lungs and magnetic resonance elastography image data is acquired while vibrations are applied to the chest wall. Shear waves are established in the gas-filled lungs by the vibrations and a shear modulus image is reconstructed from the MRE image data that may be used in the diagnosis of lung disease.

8 Claims, 5 Drawing Sheets

IMAGING ELASTIC PROPERTIES OF THE LUNG WITH MAGNETIC RESONANCE ELASTOGRAPHY

CROSS-REFERENCE TO RELATED APPLICATIONS

This application is based on U.S. Provisional Patent Application Ser. No. 60/674,818 filed on Apr. 26, 2005, and entitled "Thermally Polarized 3He Magnetic Resonance Elastography: Initial Feasibility."

STATEMENT REGARDING FEDERALLY SPONSORED RESEARCH

This invention was made with government support under Grant No. NIH EB001981, CA 91959 awarded by the National Institute of Health. The United States Government has certain rights in this invention.

BACKGROUND OF THE INVENTION

The field of the invention is nuclear magnetic resonance imaging methods and systems. More particularly, the invention relates to imaging the lungs using a noble gas such as Helium-3 or Xenon-129.

Lung disease, which includes asthma, chronic obstructive pulmonary disease (COPD), tuberculosis, and influenza is a significant and growing public health issue. In the year 2003, chronic lower respiratory disease was the fourth leading cause of death in the United States, claiming the lives of over 126,000 Americans. In contrast to mortality rates for cancer and heart disease—America's two leading causes of death, both of which decreased between 1979 and 1998—lung disease rates increased by 19.3 percent over the same interval. Not only are some lung diseases fatal, they are also chronic, affecting over 35 million Americans. Asthma and COPD account for approximately one in five cases of depression and reduced general health. Asthma affects almost 10% of the United States population, is the leading cause of pediatric hospitalizations, and has doubled in prevalence since 1980. Lung disease has a profound economic impact, costing over $141.8 billion a year in direct and indirect treatment related costs.

Within the spectrum of lung disorders, obstructive lung disease, which includes asthma and COPD, is of particular concern, accounting for approximately 35.2% of all lung related deaths in the year 2000. The mechanical properties of lung parenchyma have a fundamental role in the pathophysiology and natural history of these diseases. However, current methodologies are incapable of directly measuring these changes in vivo.

The distinct biological processes that underlie asthma and COPD, which are manifested in the macroscopic mechanical properties of lung parenchyma are not accessible by standard PV measurements. While asthma and COPD have distinct pathophysiologies, both processes produce end expiratory air trapping within the acinar units of the lung. In the asthmatic, airway smooth muscle activation, in response to a pro-inflammatory stimulus, remains central in the pathophysiology of the syndrome and it is now appreciated that 1) tissue-constriction need not be confined to the airways but may also involve contractile elements of the lung-parenchyma; 2) mucosal swelling and luminal secretions contribute significantly to reduced flows in peripheral airways; 3) peribronchial fibrosis and airway remodeling are a major cause of reduced flows in chronic asthma; and 4) all these mechanisms account to varying degrees for the large heterogeneity in regional volumes, ventilation, and mechanical properties. In COPD, while local destruction of alveoli produces a loss of parenchymal elasticity and airway enlargement, it is also appreciated that this process results in remodeling of connective tissue elements, most notably collagen, resulting in changes in the mechanical properties not only of parenchyma but also conductive airways.

Loss of tissue elasticity, particularly around airways, compromises their patency, precipitating end expiration collapse and regional air trapping. Thus, asthma and COPD present a dilemma: while both induce end-expiratory air trapping, the same volumetric condition is arrived at through dramatically different states of the mechanical properties of lung parenchyma. In asthma parenchymal stiffness remains relatively unaffected. In contrast, COPD will induce a decrease in parenchymal stiffness as a result of alveoli destruction and connective tissue element remodeling. Although changes in the expiratory phase of the quasi-static pressure-volume (PV) curve provide global insights into volumetric changes within the lung, these data cannot quantify regional pre-stress conditions which could potentially distinguish between a state of hyper inflation of normal (or asthmatic) and normally inflated emhypsemic parenchyma.

Spirometry provides a global measure of lung and airway properties. While repeated spirometry can provide insight into the volatility of the bronchi, the technique does not quantify remodeling induced changes in airway plasticity, is limited by its global nature (lacks spatial specificity), and is relatively insensitive to changes in small airway structure and function. Sputum monitoring and respiratory tests before and after the administration of bronchial dilators to assess changes in airway plasticity impose similar constraints by providing global and, at best, indirect information on spatial extent. Breath-held high speed computed tomography (CT) enables a direct visualization of the lung tissue. Unfortunately, its spatial resolution is insufficient to characterize structure and dynamics of high generation airways that are subject to remodeling. CT does provide a topographical map of gray scale distributions that may be viewed as surrogates of regional volume but regional volume information does not provide regional mechanical information and may not inform about airway remodeling. Thus CT does not differentiate between disease induced pre stress conditions arising from emphysema, asthma, and others.

Many magnetic resonance imaging (MRI) techniques have been proposed for imaging the lungs using a paramagnetic gas. A noble gas such as Xenon-13 or Helium-3 is inhaled into the lungs prior to the MRI scan to increase SNR of the acquired image. The noble gas is thermally or equilibrium polarized and is preferably hyperpolarized to produce a strong NMR signal when excited at its Larmor frequency. Imaging methods that employ paramagnetic gases are disclosed, for example, in U.S. Pat. Nos. 5,789,921; 6,241,966; 6,338,836; 6,370,415; 6,589,506 and in published U.S. Pat. Appln. Nos. 2001/0031242; 2002/0043267; 2002/0198449; 2003/0023162 and 2004/0260173.

While magnetic resonance imaging using RF tagging techniques have also been suggested as a method for assessment of the mechanical properties of parenchyma this approach is limited to assessing the change in lung volume throughout the respiratory cycle and does not assess the intrinsic mechanical properties of parenchyma. Tagged MR images of the lung will only elucidate regional changes in parenchyma inferring rather than actually measuring the intrinsic mechanical properties of parenchyma.

It has been long known that lung parenchyma exhibits elastic properties that can be quantitated by K and μ and that these parameters describe uniform inflation and isovolume deformation respectively. Ex vivo animal studies have demonstrated that in normal lungs, both K and μ are linearly related to transpulmonary pressure, $P_{tp}$ and that both parameters increase with age. In obstructive lung disease, it is generally accepted that not only the type but also the spatial distribution/heterogeneity of disease affect the intrinsic mechanical properties of lung parenchyma. Within the asthma model, both the parenchymal bulk and shear moduli have been reported to increase with bronchoconstriction in rat lung, suggesting that parenchyma stiffness should increase with asthma severity. Simulation studies have also identified the relationship between airway patency and the mechanical properties of parenchyma pointing to the relationship between regional air trapping and stiffness. Using a monoexponential model to describe the expiration phase of the respiratory PV curve, significant differences have been demonstrated in the PV curves for normal, emphysemateous, and fibrotic lungs. Because it is generally accepted that the shear modulus of lung parenchyma is related to $P_{tp}$ according to the relationship, $\mu \cong 0.7\ P_{tp}$ then disease induced changes in the PV curve translate directly to changes in the mechanical properties of lung parenchyma.

It has been found that MR imaging can be used to image the mechanical properties of tissues when an oscillating stress is applied to the object being imaged in a method called MR elastography (MRE). The method requires that the oscillating stress produce shear waves that propagate through the organ, or tissues to be imaged. These shear waves alter the phase of the NMR signals, and from this the mechanical properties of the subject can be determined. In many applications, the production of shear waves in the tissues is merely a matter of physically vibrating the surface of the subject with an electromechanical device such as that disclosed in U.S. Pat. No. 5,592,085. For example, shear waves may be produced in the breast and prostate by direct contact with the oscillatory device. As discussed in U.S. Pat. No. 5,825,186, images can be reconstructed from the acquired MRE data in which the brightness of individual pixels therein are modulated, or weighted by the stiffness of the corresponding tissue.

SUMMARY OF THE INVENTION

The present invention is a method for imaging the mechanical properties of the mammalian lung using magnetic resonance elastography, and more particularly the imaging of mechanical properties when the lung is filled with a noble gas.

It is a discovery of the present invention that shear waves can be induced into the lungs by vibrating the chest wall, and that when the lungs are filled with a paramagnetic gas such as Helium or Xenon, NMR signals can be acquired from which the mechanical properties of the lungs can be imaged. These mechanical properties provide unique opportunities for diagnosing and monitoring the progress of lung disease.

DESCRIPTION OF THE PREFERRED EMBODIMENT

Figure 1:
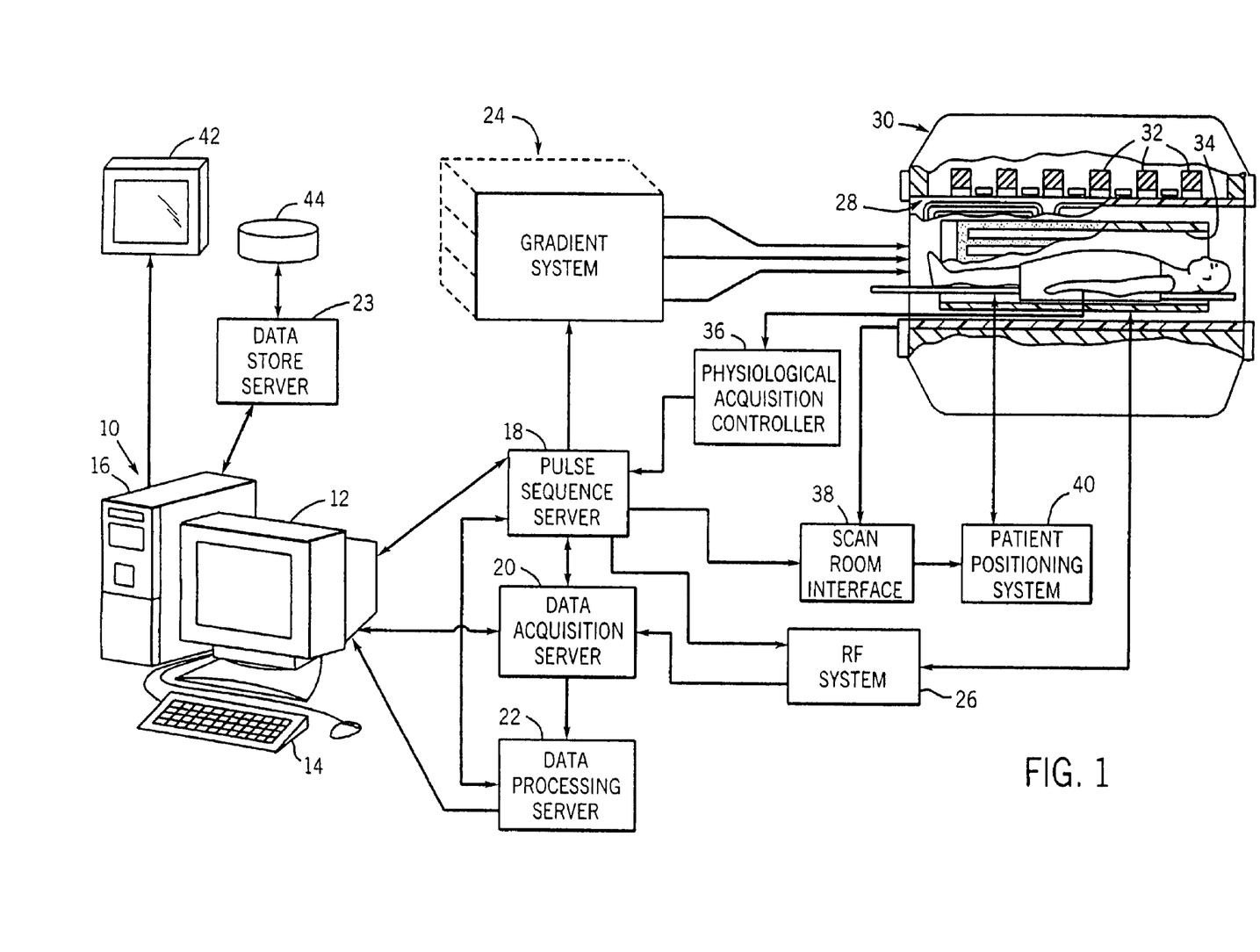
FIG. 1 is a block diagram of an MRI system which employs the present invention.

Referring particularly to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2}$$

and the phase of the received NMR signal may also be determined:

$$\Phi=\tan^{-1}Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 3:
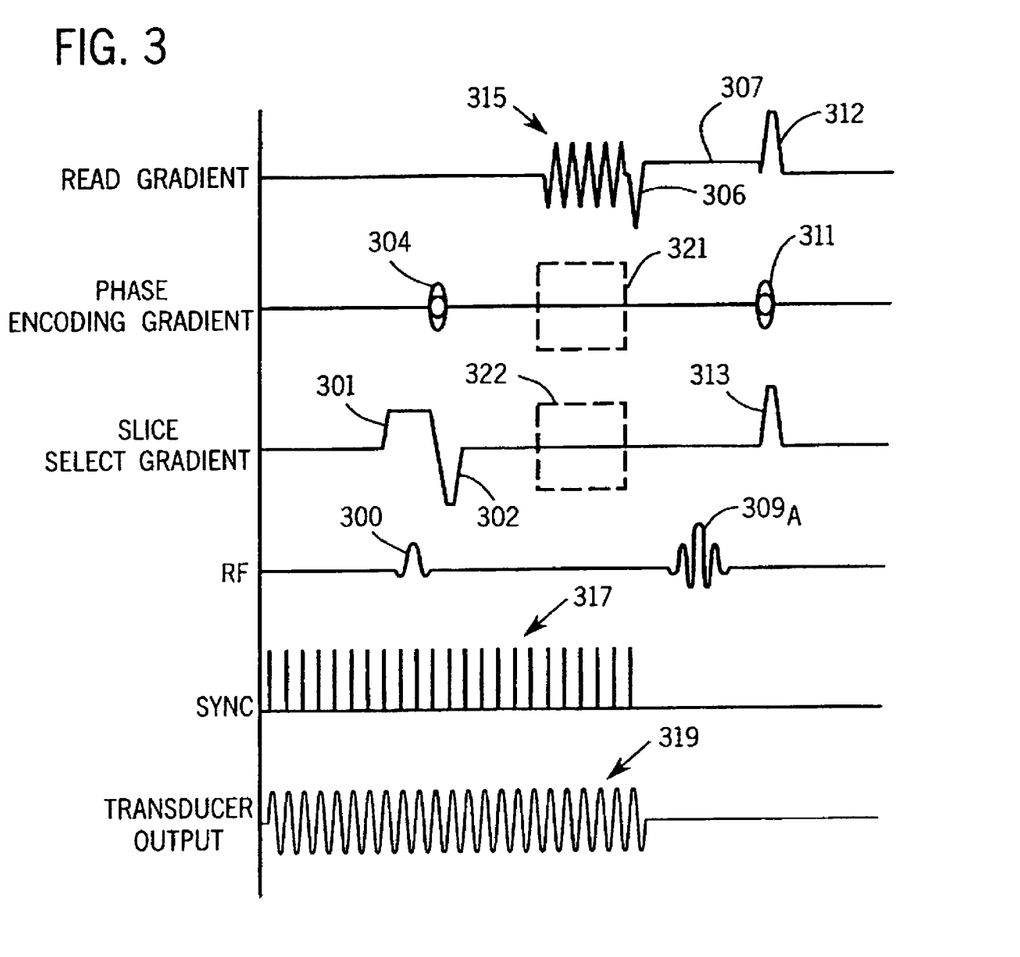
FIG. 3 is a graphic illustration of an MRE pulse sequence used to direct the MRI system of FIG. 1.

Referring particularly to FIG. 3, a preferred embodiment of a pulse sequence which may be used to acquire MRE data according to the present invention is shown. The pulse sequence is fundamentally a 2DFT pulse sequence using a gradient recalled echo. Transverse magnetization is produced by a selective 90° rf excitation pulse 300 which is produced in the presence of a slice select gradient ($G_z$) pulse 301 and followed by a rephasing gradient pulse 302. A phase encoding gradient ($G_y$) pulse 304 is then applied at an amplitude and polarity determined by the view number of the acquisition. A read gradient ($G_x$) is applied as a negative dephasing lobe 306, followed by a positive readout gradient pulse 307. An NMR echo signal 309 is acquired 40 msecs. after the rf excitation pulse 300 during the readout pulse 307 to frequency encode the 256 digitized samples. The pulse sequence is concluded with spoiler gradient pulses 312 and 313 along read and slice select axes, and a rephasing gradient pulse 311 is applied along the phase encoding axis ($G_y$). As is well known in the art, this rephasing pulse 311 has the same size and shape, but opposite polarity of the phase encoding pulse 304. The pulse sequence is repeated 128 times with the phase encoding pulse 304 stepped through its successive values to acquire a 128 by 256 array of complex NMR signal samples that comprise the data set (A). It should be apparent to those skilled in the art that many variations are possible from this preferred pulse sequence To practice the present invention an alternating magnetic field gradient is applied after the transverse magnetization is produced and before the NMR signal is acquired. In the preferred embodiment illustrated in FIG. 3, the read gradient ($G_x$) is used for this function and is alternated in polarity to produce five bipolar, gradient waveforms 315. The alternating gradient 315 has a frequency of from 50 to 200 Hz depending on the clinical application and a duration of 25 msecs. At the same time, the pulse sequence server 18 produces sync pulses as shown at 317, which are at the same frequency and have a specific phase relationship with the alternating gradient pulses 315. As will be explained below, these sync pulses 317 activate a transducer 56 to apply an oscillating stress 319 to the patient which has the same frequency and phase relationship. To insure that the resulting waves have time to propagate throughout the field of view, the sync pulses 317 may be turned on well before the pulse sequence begins, as shown in FIG. 3.

The phase of the NMR signal 309 is indicative of the movement of the spins. If the spins are stationary, the phase of the NMR signal is not altered by the alternating gradient pulses 315, whereas spins moving along the direction of the motion encoding gradient will accumulate a phase proportional to their velocity. Spins which move in synchronism and in phase with the alternating magnetic field gradient 215 will accumulate maximum phase of one polarity, and those which move in synchronism, but 180° out of phase with the alternating magnetic field gradient 215 will accumulate maximum phase of the opposite polarity. The phase of the acquired NMR signal 309 is thus affected by the "synchronous" movement of spins along the motion encoded direction.

The pulse sequence in FIG. 3 can be modified to measure synchronous spin movement along the other gradient axes. For example, the alternating magnetic field gradient pulses may be applied along the phase encoding axis as indicated by dashed lines 321, or they may be applied along the slice select axis as indicated by dashed lines 322. Indeed, they may be applied simultaneously to two or three of the gradient field directions to "read" synchronous spin movements along any desired direction.

Figure 2:
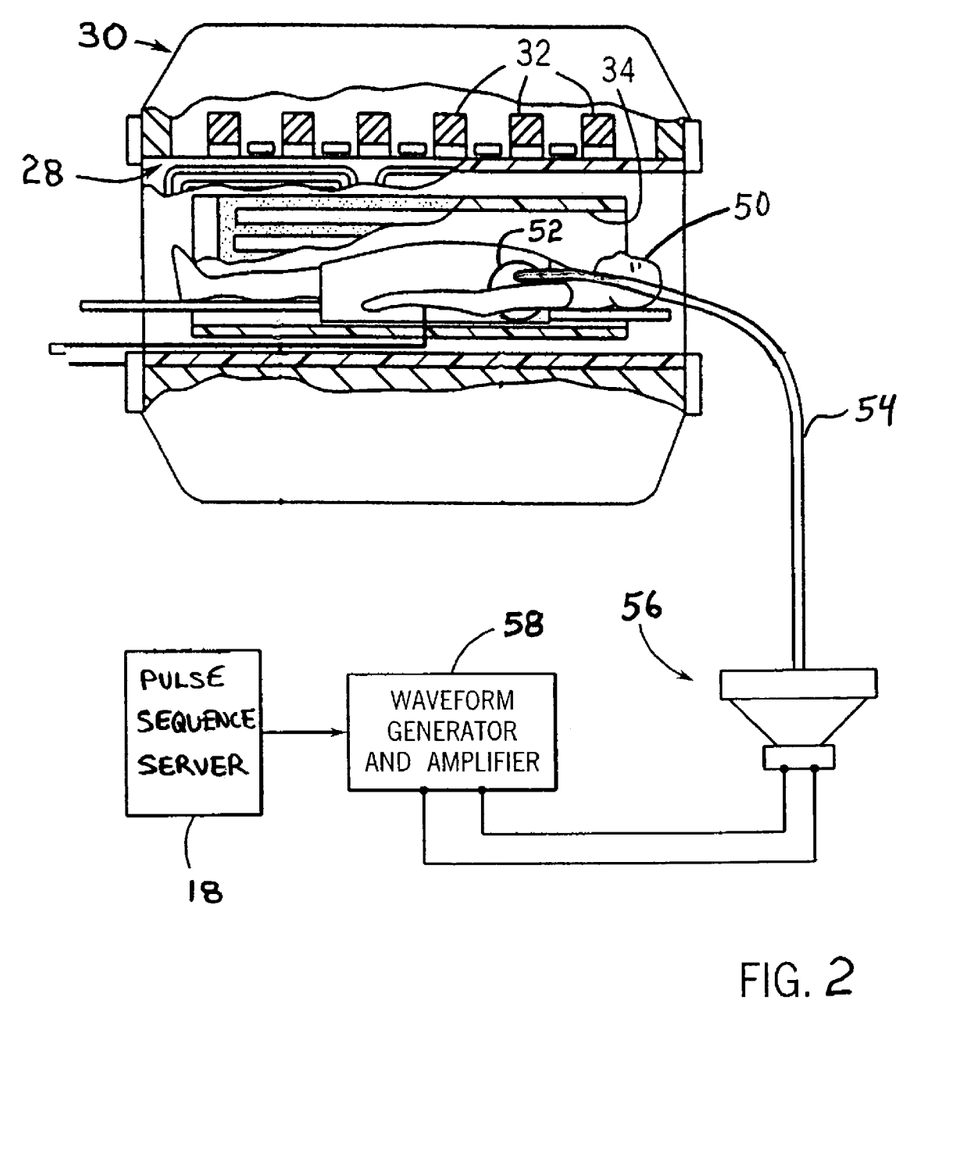
FIG. 2 is a pictorial view of the magnet and subject in FIG. 1 showing the remote driver used to apply oscillating stress to the subject's lung.

Referring particularly to FIG. 2, a subject to be examined 50 is placed in the bore of the MRI system magnet 30 and is subjected to magnetic fields produced under the direction of the pulse sequence of FIG. 3. An MRE acoustic driver such as that described in co-pending U.S. patent application Ser. No. 10/860,174 filed on Jun. 3, 2004 and entitled "Pressure Activated Driver For MR Elastography" is used to apply an oscillating stress to the subject's lungs. It includes a passive actuator 52 which is positioned over the region of interest in the subject 50 and is connected by means of a tube 54 to a remotely located driver assembly 56. The driver assembly 56 is remote from the magnet 30 in the sense that it is away from the strong magnet fields produced by the magnet 32 where its operation is not impeded by those fields, and where its operation will not perturb the MRI system magnetic fields. The driver assembly 56 is electrically driven by a waveform generator and amplifier 58, which in turn is controlled by the pulse sequence server 18.

The pulse sequence server 18 directs the MRI system to perform the above-described MRE pulse sequence, and in doing so it outputs the synchronizing pulses 317 to the waveform generator and amplifier 58. As described in the above-cited co-pending application, the sync pulses 317 enable the waveform generator 58 to produce an oscillatory signal at the proper moment during each MRE pulse sequence. This signal energizes a loudspeaker in the active driver 56 to produce acoustic waves that are coupled to the passive driver 52 through tube 54. The passive driver 52 has a membrane that is vibrated by this acoustic wave to stress tissues against which it bears.

Figure 4:
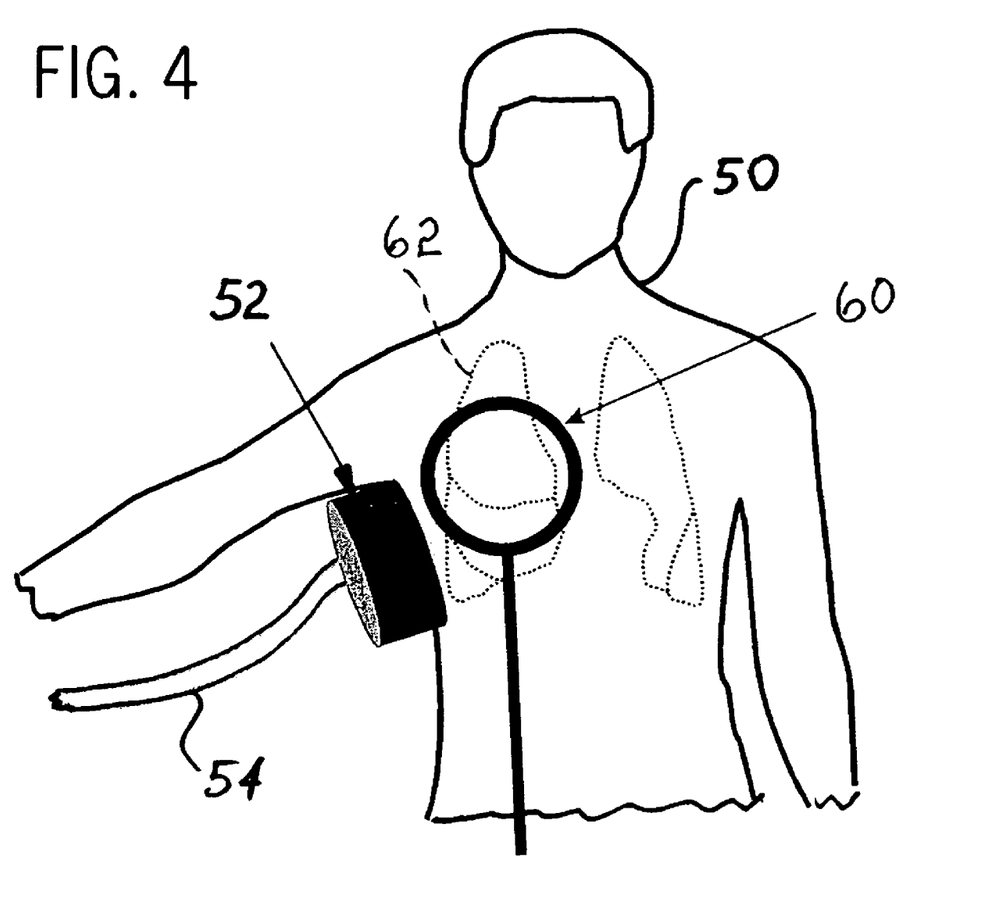
FIG. 4 is a pictorial view of the subject in FIG. 2 showing placement of a passive driver used to apply oscillating stress.

The positioning of the passive driver 52 on the subject 50 is shown best in FIG. 4. The driver 52 is placed against the axilla of the subject 50 with the driver membrane in direct mechanical contact with the skin surface. Longitudinal acoustic waves are induced medially into the subject 50 and mode converted shear waves occur at the pleural surface of the lung. These shear waves propagate into the parenchyma and produce the stress that is "seen" by the acquired MRE image.

Referring still to FIG. 4, a 5 inch diameter receive-only local rf coil 60 is positioned under the subject 50 and aligned beneath the lung 62 to be imaged. The local rf coil 60 is manufactured by General Electric Healthcare, tuned to the resonant frequency of protons at a field strength of 1.5T and equal to 63.8 MHz. Alternatively, dual tuned single channel or phased array transmit/receive coils can be used to acquire both proton and He-3 (or other gas possessing a net nuclear magnetic moment) images simultaneously.

The physical basis for measuring the elastic properties of lung parenchyma with magnetic resonance elastography (MRE) is as follows. The phase of an isochromat exposed to a time-dependent magnetic field gradient is described by the modified Larmor equation:

$$\phi(t) = \int_0^t \vec{G}_r(\tau) \cdot \vec{r}(\tau) d\tau \tag{1}$$

where $\vec{G}_r$ is the time dependent magnetic field gradient, $\vec{r}$ the position vector, and $\Phi$ the net phase accumulation, all of which are a function of the duration of the gradient field described by the time variable t. When exposed to a propagating shear wave undergoing simple harmonic motion, the position vector of the isochromat is described by the equation:

$$\vec{r}(t) = \vec{r}_o + \vec{A}_o e^{j(\vec{k} \cdot \vec{r} - \omega t + \alpha)} \tag{2}$$

where $\vec{r}_o$ is the initial position vector, $A_o$ the amplitude, $\omega$ the angular frequency, $\alpha$ the phase offset, and $\vec{K}$ the wave number of the isochromat. For the special case of a gradient field whose polarity is switched in synchronization with the propagating shear wave, substitution of equation (2) into equation (1) gives:

$$\phi(\vec{r}, \alpha) = \frac{2\gamma NT(\vec{G} \cdot \vec{A}_o)}{\pi} \sin(\vec{k} \cdot \vec{r} + \alpha) \tag{3}$$

where N is equal to the number of gradient encoding cycles and T their period. While the amplitude of the shear wave induced displacement $A_o$ is typically on the order of several microns, sensitivity to these displacements is achieved as a result of the scalar product of the gradient and displacement vectors multiplied by the term NT.

For a purely elastic material, the shear modulus is given by $\mu = \rho c^2$ or $\mu = \rho f^2 \lambda^2$ where $c = f\lambda$ is the speed of the shear wave, f is the temporal frequency of the wave, $\lambda$ its wavelength, and $\rho$ is the density of the material. If the density is considered constant, then the local shear modulus of the material can be calculated by determining the local shear wavelength from the shear wave displacement maps. For a viscous material, the shear modulus has a real part that refers to its behavior under static conditions and an imaginary part related to viscosity. We use the term shear stiffness to describe the 'effective' shear modulus at a given frequency, equal to $\rho c^2$.

By definition, the spatial wavelength, $\lambda$, is the inverse of the spatial frequency, $f_{sp}$, of the shear wave, making the equation for the shear modulus equal to:

$$\mu = \rho f_{mec}^2 / f_{sp}^2 \tag{4}$$

where $f_{mec}$ is the temporal frequency of excitation of the shear wave. This form provides a method of measuring the shear modulus by calculating the spatial frequency of the shear wave. A common technique to calculate $f_{sp}$ is local frequency estimation (LFE) as described by Manduca A, Oliphant T E, Dresner M A, et al. Magnetic Resonance Elastography: Non-Invasive Mapping Of Tissue Elasticity. Med Image Anal 2001; 5(4):237-254.

Figure 5:
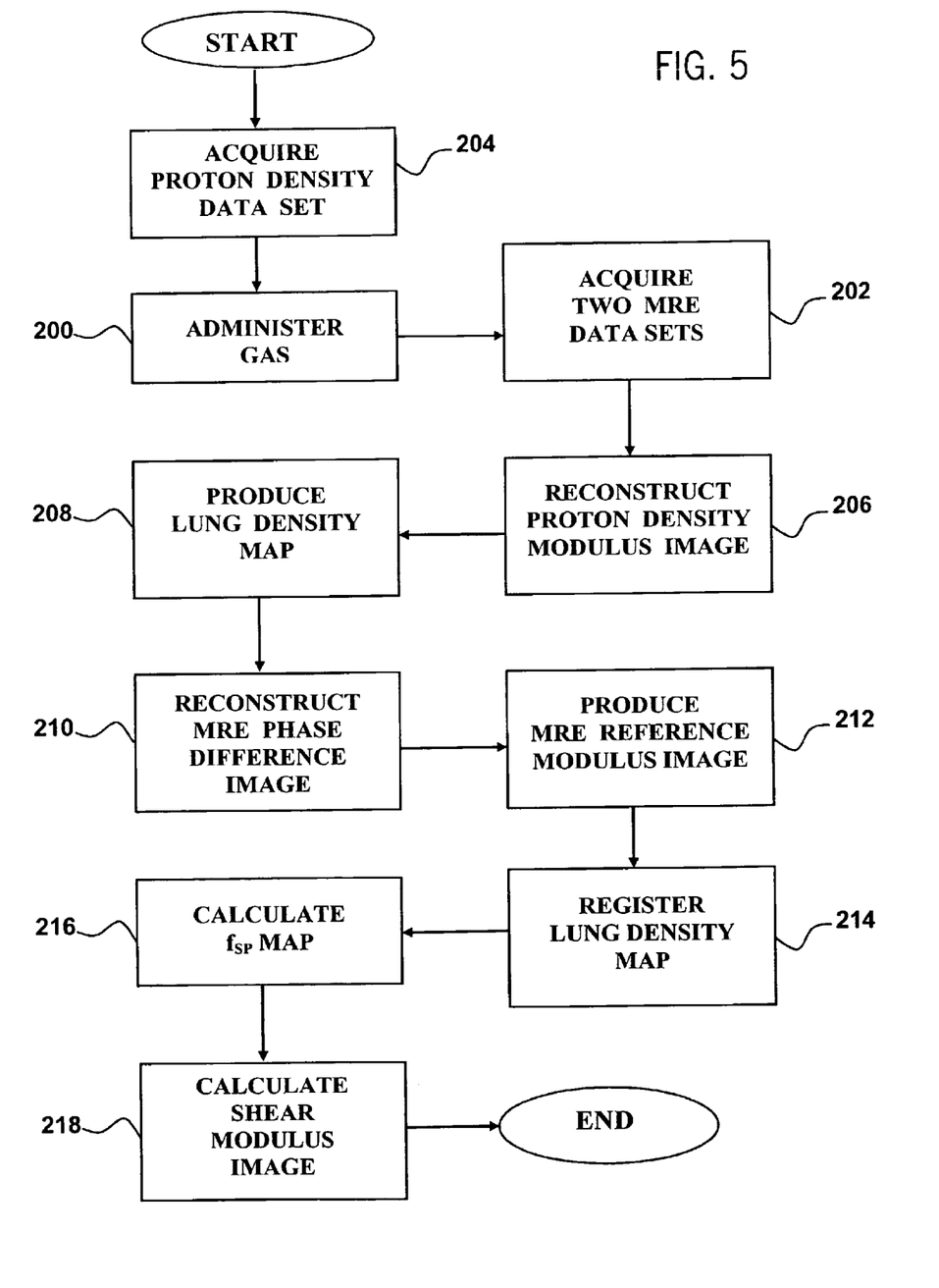
FIG. 5 is a flow chart of the steps performed with the MRI system of FIG. 1 to practice a preferred embodiment of the invention.

Referring particularly to FIG. 5, a standard proton density image is acquired as indicated by process block 204. This is done at the Larmor frequency of hydrogen and in essence it measures the density of water in the lung tissues. Since it requires more than one breath hold to acquire MRE images and the proton density image, every effort is made to maintain the subject in the same position throughout the scan and to reestablish a breath hold at the same point in the respiratory cycle. Proper re-establishment of the breath-hold is facilitated with a breath-hold monitory such as that disclosed in U.S. Pat. No. 5,363,844.

The next step in practicing the preferred embodiment of the present invention is to administer helium gas to the patient 50 as indicated at process block 200. A helium polarizer commercially available from GE Healthcare as the model IGI.9600 is used in a spin exchange optical pumping procedure to polarize 3He to 30-40%. Another option is to have the gas polarized in a central facility as described by E. J. R. van Beek, et al., "Hyperpolarized 3-helium MR imaging of the lungs: testing the concept of a central Production Facility," Eur Radiol (2003) 13:2583-2586. The technique is known as metastability-exchange optical pumping (MEOP). A dose is prepared by combining hyperpolarized 3He with nitrogen gas in a 1 L total volume that is purged and rinsed with nitrogen to remove oxygen. The dose of polarized and/or paramagnetic gas is inhaled by the subject through an attached ⅛ inch flexible tube usually starting with their lung volume at functional reserve capacity (FRC). It should be apparent that other gases with polarized nuclei or paramagnetic properties such as xenon-129 or oxygen-18 may also be used and that these gases may be polarized or hyperpolarized using known techniques to increase the NMR signals they produce. Such gases are referred to herein as "NMR responsive gases." The pulse sequence described above is then performed to acquire two MRE k-space data sets as indicated at process block 202. The first MRE data set (A) is acquired by energizing the driver 52 to produce strain waves in the subject as the MRE data is acquired. The second MRE data set is a reference data set (R) which is acquired in the same manner, but the driver 52 is not activated. Both of these data sets are acquired with the RF transmitter set to the Larmor frequency of helium and driving the whole body rf coil 34 during transmission and acquiring the NMR signals with the local coil 60.

As indicated at process block 206 a proton density modulus image is reconstructed from the acquired k-space data. This is accomplished with a standard, complex, two-dimensional Fourier transformation. The resulting I and Q values at each image pixel are combined as described above to produce the signal magnitude at each image pixel. This modulus image is then used to produce a lung density map as indicated at process block 208. This is a normalization process in which the pixels with the largest modulus signal are assumed to be non-aerated soft tissues and their values are set to 1.0. The values of the remaining pixels are scaled in magnitude accordingly such that the resulting lung density map reflects the density of the tissue at each image pixel.

The next step is to reconstruct a phase difference image from the two MRE data sets as indicated at process block 210. Each of the MRE data sets (A) and (R) are used to reconstruct an image using a complex, two-dimensional Fourier transformation and then respective A and R phase images are produced by calculating the phase at each image pixel therein using the resulting I and Q values. The reference phase image R is then subtracted from the phase image A to produce the desired phase difference image.

As indicated at process block 212 a modulus image is also produced from the reconstructed reference image R and this is used to register the lung density map with the phase difference image as indicated at process block 214. This is accomplished by shifting and rotating the proton modulus image until it aligns with the reference modulus image R and then shifting and rotating the lung density map the same amounts using one of the well-known rigid body image registration methods. If the respiration monitor is used as described above to acquire in MRE images and the proton density image at the same respiratory phase, little correction is needed.

The spatial frequency ($f_{sp}$) map may now be calculated as indicated at process block 216. As explained above, this is accomplished by making a local frequency estimation (LFE) using the phase difference image. As explained in more detail in the above cited Manduca, et al. publication, the LFE is produced at each image pixel by combining local estimates of instantaneous frequency over several scales. These estimates are derived from filters that are a product of radial and directional components and can be considered to be oriented log-normal quadrature wavelets.

The final step as indicated at process block 218 is to calculate the shear modulus image. This is done using the $f_{sp}$ map along with the registered lung density map in the above equation (4). The resulting high resolution image reveals the stiffness of the parenchyma and provides a map of the regional elastic properties of lung tissue in response to obstructive lung disease induced airway remodeling.

While the LFE method is the preferred method for estimating the local wavelength of the shear wave, other methods are possible. For example, the phase gradient method also described in the above-cited Manduca, et al. publication may be used or the algebraic inversion method described in the same publication may be used.

The invention claimed is:
1. A method for producing an image of the lung of a subject with a magnetic resonance imaging (MRI) system, the steps comprising:
   a) acquiring image data from the lung using the MRI system and a pulse sequence that solicits an NMR response from lung tissue;
   b) reconstructing a lung density map from the image data acquired in step a) that indicates the density of lung tissue at each image pixel;
   c) filling the lung with a gas that includes a NMR responsive gas;
   d) acquiring magnetic resonance elastography (MRE) image data from the lung using the MRI system and a second pulse sequence that solicits an NMR response from the NMR responsive gas;
   e) reconstructing a spatial frequency map from the MRE image data acquired in step d) that indicates frequency of a strain wave at each image pixel; and
   f) calculating a shear modulus image from the lung density map and the spatial frequency map that indicates mechanical stiffness at each image pixel.

2. The method as recited in claim 1 in which the pulse sequence used in step b) indicates the density of hydrogen protons.

3. The method as recited in claim 1 in which the NMR responsive gas is a noble gas.

4. The method as recited in claim 3 in which the NMR responsive gas is hyperpolarized helium.

5. The method as recited in claim 1 in which step d) includes;
   d)i) applying an oscillating stress to the lung at a selected frequency;
   d)ii) acquiring MRE image data with the second pulse sequence;
   d)iii) acquiring MRE reference image data with the second pulse sequence and without applying the oscillating stress; and
   step e) includes:
   e)i) reconstructing a phase image with the MRE image data acquired in step d)ii);
   e)ii) reconstructing a reference phase image with the MRE reference image data acquired in step d)iii);
   e)iii) producing a phase difference image by subtracting the reference phase image from the phase image; and
   e)iv) calculating the spatial frequency map from the phase difference image.

6. The method as recited in claim 1 in which step d) includes:

d)i) placing an acoustic device against a chest wall containing the lung;

d)ii) energizing the acoustic device during acquisition of MRE image data to produce longitudinal stress waves in the chest wall at a selected frequency.

7. The method as recited in claim 6 in which the selected frequency is in the range of 50 to 200 Hz.

8. The method as recited in claim 6 in which the acoustic driver is placed against the axilla of the subject.

* * * * *